(12) United States Patent
Lavender et al.

(10) Patent No.: US 10,709,644 B2
(45) Date of Patent: Jul. 14, 2020

(54) ORAL CARE PRODUCTS AND METHODS OF USE AND MANUFACTURE THEROF

(71) Applicant: Colgate-Palmolive Company, New York, NY (US)

(72) Inventors: Stacey Lavender, Chesterfield, NJ (US); Richard Sullivan, Atlantic Heights, NJ (US); Najma Khan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/539,192

(22) PCT Filed: Dec. 26, 2014

(86) PCT No.: PCT/US2014/072450
§ 371 (c)(1),
(2) Date: Jun. 23, 2017

(87) PCT Pub. No.: WO2016/105439
PCT Pub. Date: Jun. 30, 2016

(65) Prior Publication Data
US 2017/0354577 A1    Dec. 14, 2017

(51) Int. Cl.
*A61K 8/03* (2006.01)
*A61K 8/34* (2006.01)
*A61K 8/31* (2006.01)
*A61K 8/92* (2006.01)
*A61Q 11/00* (2006.01)

(52) U.S. Cl.
CPC ............... *A61K 8/03* (2013.01); *A61K 8/31* (2013.01); *A61K 8/345* (2013.01); *A61K 8/922* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 9,468,614 B2 | 10/2016 | Wlascliin et al. | |
| 9,622,962 B2 * | 4/2017 | Lewus | A61K 8/03 |
| 9,724,278 B2 * | 8/2017 | Lambert | A61K 8/03 |
| 2004/0247532 A1 * | 12/2004 | Pinol | A61K 8/046 424/49 |
| 2008/0311062 A1 * | 12/2008 | Dickinson | A61K 8/06 424/70.1 |
| 2009/0311200 A1 * | 12/2009 | Lambert | A61K 8/03 424/52 |
| 2011/0243856 A1 * | 10/2011 | Bartels | A61K 9/0014 424/9.8 |
| 2012/0219644 A1 * | 8/2012 | Harrington | A23D 9/007 424/727 |
| 2013/0236400 A1 | 9/2013 | Lewes et al. | |
| 2013/0298911 A1 | 11/2013 | Wlaschin et al. | |
| 2014/0106009 A1 | 4/2014 | Matheson | |

FOREIGN PATENT DOCUMENTS

| | | | |
|---|---|---|---|
| CN | 103893039 | 7/2014 | |
| EP | 1797860 A1 * | 6/2007 | A61K 8/03 |

OTHER PUBLICATIONS amazon.com, 2014, "GuruNanda Pulling Oil Oral Detox Oil Refreshing Ayurvedie Blend—8.45 fl oz.," http://www.amazon.com/GuruNanda-Pulling-Detox-Refershing-Ayurvedic/dp/B000DJDKWY.
amazon.com, 2014, "Nature's Way Liquid Coconut Oil 20 Ox.: Health & Personal Care," http://www.amazon.com/Natures-Way-Liquid-Coconut-Oil/dp/B0090PQNG6/ref=zg_bs_16320351_12.
Gardenweb, 2014, "Coconut Oil Blends," http://ths.gardenweb.com/discussions/2510999/coconut-oil-blends.
healthextermist.com, 2014, "Homemade Natural Mouthwash Recipe," http://www.healthextremist.com/homade-natural-mouthwash.
International Search Report and Written Opinion of the International Searching Authority in International Application No. PCl/US2014/072450, dated Aug. 27, 2015.
wellnessmama.com, 2014, "Does Coconut Oil Work for Oil Pulling?" http://wellnessmama.com/17951/coconut-oil-pullin.
CN103893039, Haian Yatai Additives Co Ltd., "Mouthwash," Jul. 2, 2014, English language machine translation of abstract, Espacenet, date obtained: Oct. 23, 2019, 1 page <https://worldwide.espacenet.com/publicationDetails/biblio?CC=CN&NR=103893039A&KC=A&FT=D&ND=3&date=20140702&DB=&locale=en_EP>.
He, D., et al., "Cereals & Oil Food", China Light Industry Press, pp. 616-617 (2014).
He, D., et al., "Cereals & Oil Food", China Light Industry Press, pp. 616-617 (2014), English language machine translation.

* cited by examiner

Primary Examiner — Michael P Cohen

(57) ABSTRACT

This invention relates to a dual phase mouthwash comprising a hydrophilic phase, a hydrophobic phase, and a hydrotrope, wherein the hydrophobic phase comprises coconut oil, as well as to methods of using and of making such compositions.

18 Claims, 2 Drawing Sheets

US 10,709,644 B2

ORAL CARE PRODUCTS AND METHODS OF USE AND MANUFACTURE THEROF

FIELD OF THE INVENTION

This invention relates to a dual phase mouthwash composition comprising (i) a hydrophilic phase including a hydrotrope, (ii) a hydrophobic phase, and (iii) coconut oil, as well as to methods of using and of making these compositions.

BACKGROUND OF THE INVENTION

Dry mouth, medically termed xerostomia, affects up to 20% of the population. It is a condition where the saliva in the mouth is at a deficit. Most people have experienced dry mouth at some point either due to stress, or anxiety. Prolonged symptoms of dry mouth could be due to an underlying medical disease, such as diabetes, or doe to the usage of certain medications. Symptoms include a perceived feeling of stickiness or dryness in the oral cavity, trouble chewing, swallowing, or tasting of food. Dry mouth symptoms could also include cracked lips, dry tongue, mouth sores or oral infections.

Saliva plays an important function in the oral cavity. It has an essential role in protecting, and lubricating the oral mucosa. The lubricating properties of saliva provide comfort and help protect the oral tissues against ulcers, sores, and other effects of friction. Saliva neutralizes acids and provides antibodies against bacterial threat. Saliva also aids in the digestion of food and the remineralization of enamel. Saliva is also a critical contributor to a person's ability to taste, as it acts as a solvent for the taste stimuli. Decreased salivation could lead to many oral problems, such as tooth decay, and oral infections.

Treatment for dry mouth most often includes products that are saliva substitutes or incite saliva stimulation. Saliva substitutes are used to replace the mucoadhesive, lubricative, and protective function of saliva. They commonly consist of biopolymers or polysaccharides to try to replicate the viscoelastic properties of saliva and most often result in the delivery of a very thick formulation perceived by the consumer.

Coconut oil, a natural vegetable oil, is used in many personal care applications as a skin moisturizer. It shares many properties that a lubricant should have such as 1) high viscosity index 2) good lubricity 3) high flash point and 4) low evaporative loss. Vegetable oils in general are considered good boundary lubricants in that they give rise to very low coefficient of friction. Though coconut oil is more stable than other vegetable oils, it is not as widely used as a lubricant because of its congelation temperature; i.e., because it is a solid at room temperature.

There exists a need for consumer friendly dry mouth products that, can lubricate and moisturize the oral cavity providing relief and comfort to the oral mucosa.

BRIEF SUMMARY OF THE INVENTION

It has surprisingly been found that coconut oil can be employed in a two-phase system to provide a mouthrinse that delivers oral moisturization and lubrication. In some embodiments, the invention provides a two-phase mouthrinse that comprises an oil layer and an aqueous layer, wherein the oil layer includes coconut oil. In preferred embodiments, the mouthwash is prepared by a process wherein the coconut oil is dispersed in a hydrophobic phase comprising an oil, and the mixture is combined with the hydrophilic phase to produce a stable and effective composition.

The invention thus encompasses oral care compositions and methods of using the same that are effective in delivering oral moisturization and lubrication. The invention also encompasses compositions and methods to treat dry mouth, and to clean and lubricate the oral cavity, including the lips, and provides improved methods of promoting oral health and/or systemic health, including cardiovascular health, e.g., by treating, relieving or reducing dry mouth, reducing or inhibiting gingivitis, promoting healing of sores or cuts in the mouth, inhibiting microbial biofilm formation in the oral cavity, reducing erosion of the teeth, immunizing teeth against cariogenic bacteria and their effects, and/or moisturizing the lips and/or mouth.

The invention thus provides a mouthwash composition (a Composition of the Invention), comprising (i) a hydrophilic phase; (ii) a hydrophobic phase comprising at least two oils, one of the oils being coconut oil; and (in) a hydotrope component; wherein the mouthwash is prepared by a process comprising the steps of:

a) dispersing coconut oil in a hydrophobic composition comprising an oil to form a mixture; and b) combining the mixture with the hydrophilic phase and the hydrotrope component. In some embodiments, the hydrophobic phase comprises coconut oil and another oil, for example mineral oil; and the hydrophilic phase comprises the hydrotrope component.

The Compositions of the invention may comprise additional ingredients, e.g., selected from one or more of water, a fluoride ion source, surfactants, solvents, vitamins, minerals, polymers, enzymes, humectants, thickeners, additional antimicrobial agents, additional preservatives, flavorings, colorings and/or combinations thereof. In particular embodiments, the invention may comprise an antimicrobial agent; a fluoride ion source; and an organic acid, for example citric acid.

The invention further encompasses methods comprising applying compositions effective upon application to the oral cavity, e.g., rinsing the oral cavity, optionally in conjunction with brushing, to (i) treat, relieve or reduce dry mouth, (ii) moisturize the oral cavity and lips, (iii) promote healing of sores or cuts in the mouth, (iv) clean the teeth and oral cavity, (v) reduce erosion, (vi) reduce or inhibit demineralization and promote remineralization of the teeth, (vii) reduce or inhibit, gingivitis, and (viii) inhibit microbial biofilm formation in the oral cavity.

DETAILED DESCRIPTION OF THE INVENTION

Figure 1:
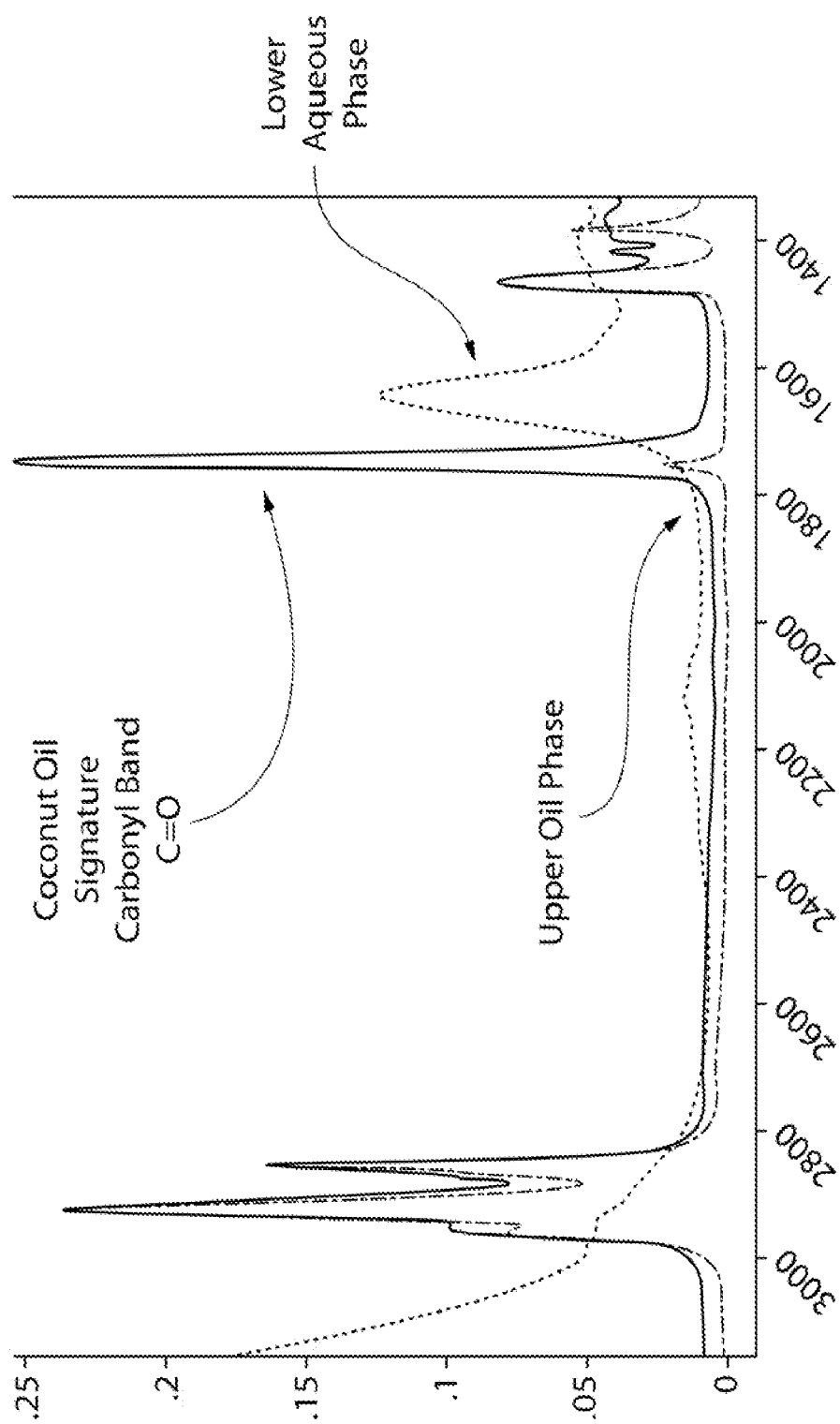
FIG. 1 shows the IR spectra for the hydrophobic and hydrophilic phases of a composition of the invention.

The invention thus provides, in a first embodiment, a dual phase mouthwash (Composition 1.0), comprising:

a hydrophilic phase;

a hydrophobic phase comprising at least, two oils, one of said oils being coconut oil; and a hydrotrope component;

wherein the mouthwash is prepared by a process comprising the steps of:

a) dispersing coconut oil in a hydrophobic composition comprising an oil to form a mixture; and b) combining the mixture with the hydrophilic phase and the hydrotrope component.

For example, any of the following compositions:

1.0.1. Composition 1.0, wherein the coconut oil is present in an amount of from 0.05% to 2%, e.g., 0.1% to 1%, by weight of the composition.

1.0.2, Composition 1.0 or 1.1, wherein the wherein hydrophobic and hydrophilic phases spontaneously separate following mixing of the phases and are substantially non-emulsified at room temperature one hour following mixing; or 30 minutes, following mixing; or at 10 minutes following mixing; or at 5 minutes following mixing; or at 1 minute following mixing; or at 30 seconds following mixing.

1.0.3. Any of the foregoing compositions wherein the hydrotrope component of the hydrophilic phase comprises one or more of glycerin, sorbitol, a polyglycol, a polyhydric alcohol, or a pyrrolidone.

1.0.4. Any of the foregoing compositions wherein the hydrotrope component comprises one or more of glycerin, sorbitol, a pyrrolidone, ethylene glycol, propylene glycol, diethylene glycol, di-propylene glycol, tripropylene glycol, xylene glycol, 1,3-butylene glycol 1,4-butylene glycol, 1,2,6-hexanetriol, xylitel, or a combination of two or more thereof.

1.0.5, Any of the foregoing compositions wherein the hydrotrope component of the hydrophilic phase comprises glycerin and sorbitol.

1.0.6. Any of the foregoing compositions wherein the hydrophobic phase comprises an oil selected from liquid paraffin (mineral oil), isopropyl myristate, an edible oil, edible oils such as olive oil, corn oil, coconut oil, soybean oil, silicon oils, palm oil, avocado oil, flax/linseed oil, canola/rapeseed oil, peanut oil, sunflower oil, sesame oil, safflower oil almond oil, grapeseed oil, and combinations thereof.

1.0.7. Any of the foregoing compositions wherein the hydrophilic phase comprises the hydrotrope component.

1.0.8. Any of the foregoing compositions further comprising a preservative, or example in amount of from 0.05% to 0.5% by weight.

1.0.9. Any of the foregoing compositions wherein the hydrophilic phase is from 1% to 90% of the composition by volume.

1.0.10. Any of the foregoing compositions wherein the hydrophobic phase is from 5% to 20% of the composition by volume.

1.0.11. Any of the foregoing compositions wherein the ratio of the weight of the hydrophilic phase to hydrophobic phase is from 1:1 to 20:1, for example of from 1:1 to 10:1; for example from 3:1 to 7:1; for example from 5:1 to 6:1; for example 5.5 to 1. In some embodiments, the compositions comprise about 10% to 15%, for example 13% oil phase; and about 68% to 74%; for example 71%, aqueous phase by weight.

1.0.12. Any of the foregoing compositions wherein the hydrophilic phase further comprises an antibacterial (antimicrobial) agent, selected from halogenated di phenyl ether (e.g. triclosan), herbal extracts and essential oils (e.g., rosemary extract, tea extract, magnolia extract, thymol, menthol, eucalyptol, geransol, carvacrol, cifral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidme), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., zinc salts, for example zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; in an effective amount, for example from 0.01-0.1%, e.g., 0.05%-0.075% by weight.

1.0.13. Any of the preceding compositions further comprising a fluoride source, e.g., a fluoride salt, for example sodium fluoride, or wherein the fluoride is covalently bound to another atom, e.g., a monofluorophosphaie, for example sodium monofluorophosphate, a fluorosilicate, e.g., sodium fluorosisicate or ammonium fluorosilicate, or aftluorosulfate, e.g., hexafluorosulfate, amine fluoride and combinations thereof.

1.0.14. The preceding composition wherein the fluoride salt is present in an amount to provide 1 to 2000 ppm, for example 100 to 250 ppm available fluoride.

1.0.15. Any of the preceding compositions comprising sodium fluoride in an amount of 0.01-0.1%, e.g., 0.05%.

1.0.16. Any of the foregoing compositions further comprising one or more of humectants, flavorings, sweeteners, sensates and/or odor neutralizing agents.

1.0.17. Any of the foregoing compositions wherein the hydrophilic phase comprises an effective amount of a preservative.

1.0.18. Any of the foregoing compositions wherein the hydrophilic phase further comprises an acid, e.g. an organic acid. i.e., citric acid.

1.0.19. Any of the preceding compositions comprising a fat-soluble vitamin or antioxidant, foe example one or more of Co-enzyme Q10, Vitamin E, Vitamin A, Vitamin D and Vitamin K.

1.0.20. Any of the foregoing compositions wherein the hydrotrope component comprises glycerin and sorbitol, each in an amount of from 5%-10% by weight.

1.0.21. Any of the foregoing compositions wherein the hydrophobic phase comprises coconut-oil in an amount of from 0.05%-2% by weight; and mineral oil, silicon oil or mixtures thereof, in an amount of from 5%-15% by weight.

1.0.22. Any of the foregoing compositions further comprising a preservative in amount of from 0.05% to 0.5% by weight; an optional antibacterial agent, in an amount of from 0%-0.1%, e.g., 0.05%-0.075% by weight; an optional fluoride ion source, e.g. sodium fluoride; and citric acid in an amount, e.g., of from 0.01% to 0.05% by weight.

1.0.23. Any of the foregoing compositions further comprising an agent that interferes with or prevents bacterial attachment, e.g., solbrol or chitosan.

1.0.24. Any of the foregoing compositions effective upon application to the oral cavity, e.g., by rinsing, optionally in conjunction with brushing, to (i) reduce or inhibit gingivitis, (ii) promote healing of sores or cuts in the mouth, (iii) inhibit microbial biofilm formation in the oral cavity, (iv) treat, relieve or reduce dry mouth, (v) clean the teeth and oral cavity (vi) promote systemic health, including cardiovascular health, e.g., by reducing potential, for systemic infection via the oral tissues.

1.0.25. Any of the foregoing compositions wherein the two phases are distinct and clear at room temperature.

1.0.26. Any of the foregoing compositions, wherein the hydrophobic and hydrophilic phases spontaneously separate following mixing of the phases to form two clear and distinct layers at room temperature within 1 minute following mixing; and preferably at 30 seconds following mixing.

1.0.27. A composition obtained or obtainable by combining the ingredients as set forth in any of the preceding compositions.

Levels of active ingredients will vary based on the nature of the delivery system and the particular active. For example, the coconut oil may be present at levels from, e.g., 0.05% to 2%, e.g., 0.1% to 1% by weight. Fluoride may be present at levels of e.g., 25 to 250 ppm, or up to 10× higher for a professional or prescription treatment product. Levels of antibacterial will vary similarly, depending on the agent used.

In another embodiment, the disclosure provides a method for treating dry mouth comprising contacting the oral cavity of a mammal having dry mouth with a composition 1.0 et seq. as described herein. In a further embodiment, a method is provided for moisturizing the lips of a mammal, comprising contacting the lips of the mammal with a composition 1.0 et seq. as described herein. In a further embodiment, a method is provided for lubricating the oral cavity of a mammal comprising contacting the oral cavity of the mammal with a composition 1.0 et seq. as described herein.

In another embodiment, the invention encompasses a method to improve oral health comprising applying an effective amount of the oral composition of any of the embodiments set forth above to the oral cavity of a subject in need thereof e.g., a method to:

a. reduce or inhibit gingivitis,
b. promote healing of sores or cuts in the mouth,
c. inhibit microbial biofilm formation in the oral cavity,
d. treat, relieve or reduce dry mouth,
e. enhance systemic health, including cardiovascular health,
f. reduce erosion of the teeth,
g. to immunize the teeth against cariogenic bacteria and their effects, and/or
h. clean, the teeth and oral cavity.
i. moisturize the mouth and/or lips,
j. reduce or inhibit demineralization and promote remineralization of the teeth.

In a further embodiment, the disclosure provides a method for preparing a dual phase mouthwash comprising: dispersing coconut oil in a hydrophobic composition comprising an oil, to form a hydrophobic mixture; and combining the hydrophobic mixture with an aqueous hydrophilic composition and a hydrotrope component.

The invention further comprises the use of coconut, oil in the manufacture of a Composition of the Invention, e.g., for use in any of the indications set forth in the above method.

The compositions of the invention are intended to be mixed and then poured for use as a normal mouthrinse, delivering a dose of the coconut oil to relieve dry mouth symptoms, as well as other added actives. The aqueous layer can also be used as a vehicle to deliver additional water soluble ingredients that also may aid in the relief of dry mouth symptoms and other conditions of the oral, cavity.

The compositions of the present invention comprise a hydrophilic and a hydrophobic phase, and a hydrotrope component which when mixed form a temporary oil in water emulsion, which spontaneously breaks down and separates back into the hydrophobic and hydrophilic phases, in some preferred embodiments, the hydrophobic and hydrophilic phases spontaneously separate following mixing of the phases, and are substantially non-emulsified at room temperature one hour following mixing; or 30 minutes following mixing; or at 10 minutes following mixing: or preferably at 5 minutes following mixing; more preferably at 1 minute following mixing; and more preferably at 30 seconds following mixing. Thus, in some preferred embodiments, after mixing, the hydrophobic and hydrophilic phases spontaneously separate into two distinct layers within the above-mentioned time periods; preferably within 11 minute, more preferably within 30 seconds of cessation of mixing. In some preferred embodiments, the two distinct layers, which may have a color, are nevertheless clear—i.e., they are not cloudy, and while they may still contain bubbles that have not yet dissipated, they are substantially devoid of visually detectable particulates at room temperature.

The hydrophobic phase of the composition of the present invention may contain any orally acceptable hydrophobic liquid, e.g., generally recognized as safe. Such materials are known in the art, and may include isopropyl myristate, liquid paraffin (mineral oil), edible oils such as olive oil, corn oil, coconut oil, soybean oil, silicon oils, palm oil, avocado oil, flax/linseed oil canola/rapeseed oil, peanut oil, sunflower oil, sesame oil, safflower oil, almond oil, grapeseed oil, and combinations thereof. A preferred hydrophobic phase comprises liquid paraffin (mineral oil). Preferably, the hydrophobic phase has a HLB of from 7 to 12, e.g., 10.

The hydrophilic phase of the compositions of the present invention are aqueous based, e.g., having from 40% to 95% by weight water. Other useful materials may also include orally acceptable alcohols, humectants, or polymers. A humectant on a pure humectant basis, generally includes 10% to 50% in one embodiment or 15% to 25% in another embodiment by weight of the mouth wash composition. The hydrophilic phase may optionally include one or more polymers, e.g., in the hydrophilic phase, such as polyvinyl-methyl ether maleic acid copolymers, polysaccharides (e.g. cellulose derivatives, for example carboxymethyl cellulose, or polysaccharide gums, for example xanthan gum or carrageenan gum). The compositions of the present invention may contain an orally acceptable polyvinylmethylether/maleic anhydride (PVME/MA.) copolymer. The PVME/MA copolymer is present from 0.1% to 20%, for example 0.5% to 10% by weight. Generally the methyl vinyl ether to maleic anhydride ratio in the copolymer is 1:4 to 4:1, and the copolymer has an average molecular weight of 30,000 to 1,000,000, for example 30,000 to 500,000. Preferred PVME/MA copolymers include those under the GANTREZ brand from ISP (Wayne, N.J.). The PVME/MA copolymer may also act as an antibacterial enhancing agent if present in an antibacterial enhancing effective amount.

Hydrotropes are known in the art, and include compounds that solubilize hydrophobic compounds in aqueous solutions. Hydrotropes are low molecular weight ampiphilic compounds which resemble surfactants in as much as they have hydrophilic groups, and, in surfactant terms, what may be described as a low molecular weight hydrophobe. The hydrophilic group is may be attached to an organic moiety that is too short a group to confer true surface active properties. Hydrotropes useful in the present invention include glycerin and sorbitol, and mixtures thereof, and also may include aromatic sulfonates, aromatic phosphate esters, di and polycarboxylates, polyglycols, and alcohols, including polyhydric alcohols. Hydrotropes used in the present invention have a HLB value of from 7 to 18. Although any hydrotrope may be useful in the present invention, the hydrotrope may have a HLB value similar to that of the hydrophobic phase, and thus, the exact hydrotrope useful in the compositions will be dependent upon the composition of the hydrophobic phase. Preferably, the HLB of the coupling system is greater than the HLB of the hydrophobic phase, e.g., 10%, 15%, 20%, or 30% greater than the HLB of the hydrophobic phase. Methods of determining HLB is well known to those of skill in the art. The hydrotrope component in the present invention comprises one or more polyglycols and/or polyhydric alcohols, preferably a diol and/or a triol. Preferably, the coupling system comprises glycerin and sorbitol. The exact ratio of glycerin and sorbitol in the coupling system will depend on the desired HLB of the hydrotrope component of the present invention. As the hydrotrope lacks surfactant properties, the dispersion of the oil phase in the water is not thermodynamically stable, and an emulsion formed by mixing the two phases reverts back into separate and distinct phases immediately following mixing.

Coconut oil is a solid at room temperature. When added to water or aqueous formulations, it tends to form solid particulates. Applicants have surprisingly discovered that coconut oil can be formulated into a two-phase mouthwash that rapidly separates into two distinct and clear phases alter mixing at room temperature, by first dispersing the coconut oil in a hydrophobic composition comprising an oil, for example in mineral oil, to form a mixture, and then combining the mixture with the aqueous components of the mouthwash. As used herein, dispersing the coconut oil in a hydrophobic composition comprising an oil to form a mixture is intended to mean the combining together of the coconut oil and at least an oil component of the hydrophobic phase to provide a solution.

In one embodiment of the present invention, the oral compositions are free, or substantially free of surfactants, especially anionic, cationic, and zwitterionic surfactants. Nonionic surfactants may be use in limited quantities in the present invention, provided that they do not interfere with the ability of the hydrophobic and hydrophilic phases to spontaneously separate following mixing of the phases, to substantially non-emulsify at room temperature within the time periods specified above.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Preservatives; A wide variety of preservatives can be used in the compositions of the invention.

Suitable preservatives include, for example, sodium benzoate, potassium sorbate, methylisothiazolinone, paraben preservatives, for example methyl p-hydroxybenzoate, propyl p-hydroxybenzoate, and mixtures thereof.

Flavoring Agents:

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as, for example and not limitation, sodium saccharin and sucralose. Examples of the essential oils include oils of spearmint, peppermint, wintergreen, sassafras, clove, sage, eucalyptus, marjoram, cinnamon, lemon, lime, grapefruit and orange. Also useful are such chemicals as menthol, carvone, and anethole. Certain embodiments employ the oils of peppermint and spearmint. The flavoring agent is typically incorporated in the oral composition at a concentration of 0.01 to 1.5% by weight.

Anti-Calculus Agents:

In some embodiments, the oral compositions of the present invention comprise antitartar agents to prevent and/or minimize calculus formation. One or more of such agents can be present. Suitable anticalcolus agents include without limitation: stannous, copper, magnesium and strontium salts, dimethicone copolvols such as cetyl dimethicone copolyol, glucoamylase, glucose oxidase, urea, calcium lactate, calcium glycerophosphate, strontium polyacrylates and chelating agents such as citric and tartaric acids and alkali metal salts thereof, and salts of EDTA, for example tetrasodium EDTA; and phosphates and polyphosphates. Phosphate and polyphosphate salts are generally employed in the form of their wholly or partially neutralized water soluble catianic species (e.g., potassium, sodium or ammonium salts, and any mixtures thereof). Thus, useful inorganic phosphate and polyphosphate salts illustratively include monovalent cations with monobasic, dibasic and tribasic phosphates; tripolyphosphate and tetrapolyphosphate; mono-, di-, tri- and tetra-pyrophosphates; and cyclophosphates (also generally known in the art as "metaphosphates"). Useful monovalent cations of such phosphate salts include hydrogen, monovalent metals including alkali metals, and ammonium, for example.

Sensates:

In some embodiments, the oral compositions of the present invention comprise one or more sensates—i.e., ingredients which impart some kind of sensation to the oral cavity. Suitable sensates include without limitation, Suitable sensates in include physiological cooling agents including 1-menthol and 3-(1-menthoxy)propane-1,2-diol, peppermint oil, N-substituted-p-menthane-3-carboxamides, acyclic tertiary and secondary carboxamides, and 3-1-menthoxy propan-1,2-diol (see, e.g., PCX Published Application Number WO 97/06695); heating and/or wanning sensates such as, for example and not limited to, vanillyl alcohol n-butyl ether (vanillyl butyl ether), vanillvl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, connamic aldehyde and phosphate derivatives of same; materials that are known to cause a tingling, numbing and/or stinging sensation and are used in foods as popular spice and/or herb condiments; and combinations thereof.

Odor Neutralizing Agents; In some embodiments, the oral compositions of the present invention comprise one or more odor-neutralizing agents.

Suitable odor neutralizing agents include, without limitation, chlorine dioxide; peroxides such a hydrogen peroxide; chlorite salts and bicarbonate salts, —e.g. sodium chlorite and sodium bicarbonate; essential oils such as eucalyptol, menthol, methyl salicylate and thymol; flavor cocktails; and zinc salts such as, for example and not limited to, zinc chloride, zinc citrate, zinc acetate, zinc sulfate, and zinc phenolsulfate.

Water:

Water is present in the oral compositions of the invention. Water, employed in the preparation of commercial oral compositions should be deionized and free of organic impurities. Water commonly makes up the balance of the compositions and includes 10% to 90%, e.g., 40% to 80%, e.g., 70% to 80% by weight of the oral compositions. This amount of water includes the free water which is added plus that amount which is introduced with other materials such as with sorbitol or any components of the invention.

Humectants:

Within certain embodiments of the oral compositions, it is also desirable to incorporate a humectant to reduce evaporation and also contribute towards preservation by lowering water activity. Certain humectants can also impart desirable sweetness or flavor to compositions. The humectant, on a pure humectant basis, generally includes 15% to 70% in one embodiment or 30% to 65% in another embodiment by weight of the composition.

Suitable humectants include edible polyhydric alcohols such as glycerin, sorbitol, xylitel, propylene glycol as well as other polyols and mixtures of these humectants. Mixtures of glycerin and sorbitol may be used in certain embodiments as the humectant component of the compositions herein.

As will be evident to one of skill in the art, some components of the invention may perform multiple functions, and the identification of a compound as having one function herein is not meant to exclude its use for other functions in a particular composition. For example, a compound such as glycerin or sorbitol may function in the hydrotrope component, but also act as a humectant.

The present invention in its method aspect involves applying to the oral cavity a safe and effective amount of the compositions described herein.

The compositions and methods according to the invention are useful, inter alia, to lubricate the oral cavity of a mammal, for example a human, and in particular to clean and lubricate the oral cavity and provide improved methods of promoting oral health and/or systemic health, including cardiovascular health, e.g., by treating, relieving or reducing dry mouth.

Enhancing oral health also provides benefits in systemic health, as the oral tissues can be gateways for systemic infections. Good oral health is associated with systemic health, including cardiovascular health. The compositions and methods of the invention are thus useful to enhance systemic health, including cardiovascular health.

As used throughout, ranges are used as shorthand for describing each and every value that, is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Representative Formulation of the Invention

Table 1 below shows representative formulations according to the invention.

TABLE 1

| Ingredient | Weight % Range |
|---|---|
| DI Water | 71-74 |
| Coconut Oil | 0.05-2 |
| Mineral Oil | 5-15 |
| Dye | 0.0005-1.5 |
| Flavor | 0.5-1.5 |
| Anti-bacterial agent | 0-0.075 |
| Sodium Flouride | 0-0.05 |
| Glycerin | 5-10 |
| Sorbitol | 5-10 |
| Preservative | 0.05-0.5 |
| Citric Acid | 0.01-0.05 |
| Silcone | 0-0.01 |
| Sweetner | 0.05-0.1 |
| Sensate | 0-0.1 |
| Odor Neutralizing Agent | 0-0.1 |

A stable, two-phase composition was prepared as described below in Table 2.

TABLE 2

| Ingredient | Weight % Range |
|---|---|
| Water | 71.387 |
| Hydrogenated Coconut Oil | 1.0 |
| Mineral Oil | 13.0 |
| FD&C Blue #1 | 0.0006 |
| Flavor | 1.4 |
| Glycerin | 7.5 |
| Sorbitol | 5.5 |
| Potassium Sorbate | 0.1 |
| Citric Acid | 0.03 |
| Sucralose | 0.002 |
| Sodium Saccharin | 0.08 |

The coconut oil was dispersed in the hydrophobic (i.e., mineral oil) phase. Coconut oil is not water soluble, and forms solid particulates when added to directly to water or aqueous formulations. Incorporation of coconut, oil into a dual phase mouthrinse as described above prevents the coconut oil from solidifying in the formulation and results in a composition that is effective for the relief of dry mouth symptoms.

Upon mixing, the mouthwash forms a temporary emulsion, and spontaneously reverts back to the two original phases after rest, without the formation of an emulsion. FIG. 1 shows IR spectra for the hydrophilic (aqueous) and hydrophobic (oil) phases of the composition. It can be seen that the characteristic carbonyl (C=O) band peak of the coconut oil is located in the oil phase, indicating that the coconut oil is partitioned into that phase.

Figure 2:
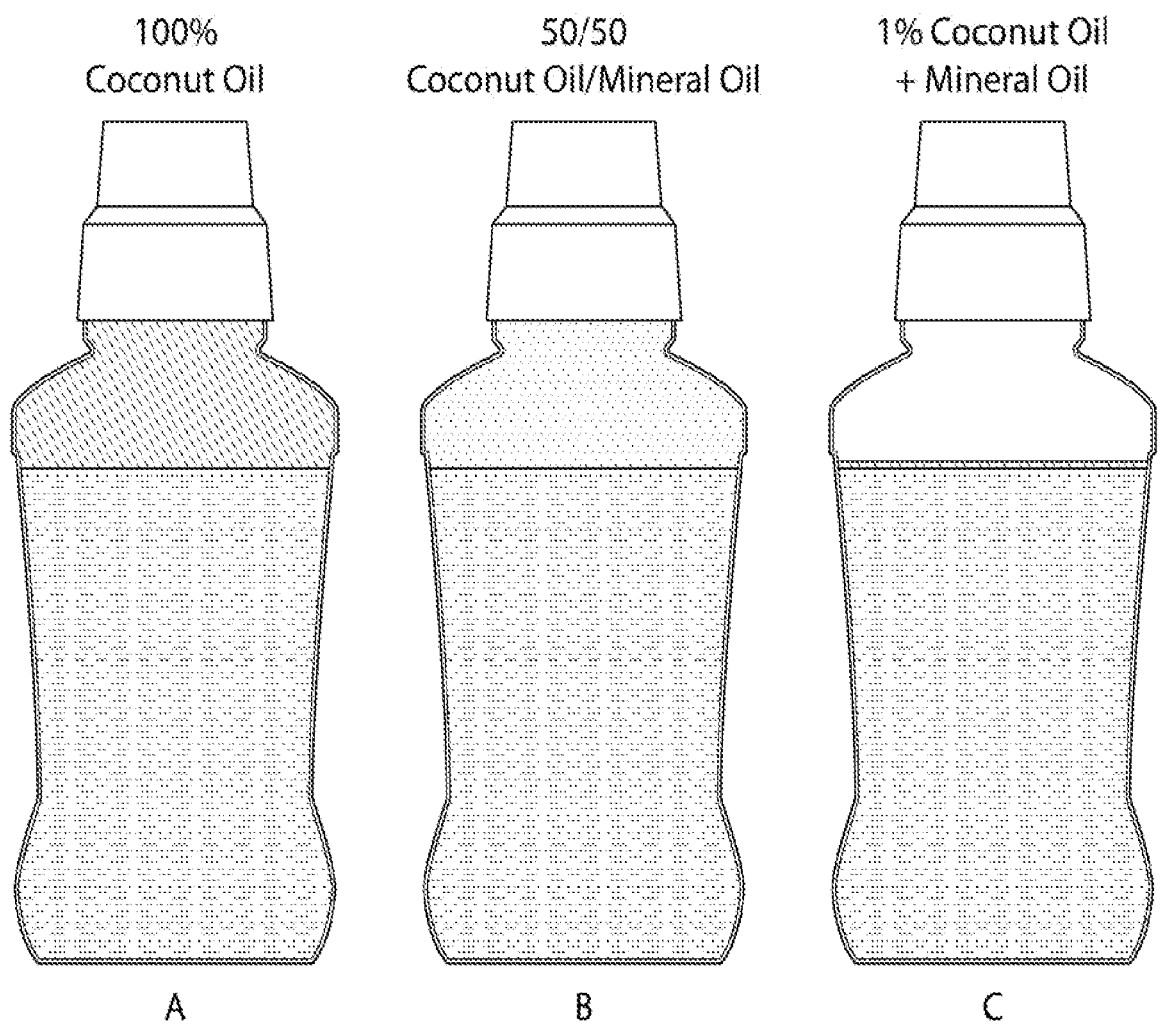
FIG. 2 shows a comparison of formulations having different amounts of coconut oil in the oil layer.

FIG. 2 shows a comparison of formulations having different amounts of coconut oil in the oil layer. Formulations A, B and C each contain a hydrophilic layer and hydrotrope as described in Table 1 above. Formulation A contains 100% coconut oil (13% Coconut Oil in final formulation) as the oil (i.e., hydrophobic) layer. Formulation B contains 50% coconut oil (6.5% final Coconut Oil in formulation) in mineral oil as the oil layer, and Formulation C contains 1% coconut oil (in final formulation) in mineral oil as the oil layer as the oil layer. It can be seen that one hour following mixing, Formulation A separates to yield the 100% coconut oil in a solid layer; the 50% coconut oil layer incompletely separates to produce a cloudy oil layer, and the 1% coconut oil layer fully separates to yield two clear and distinct phases. Thus, the amount of coconut oil is a significant factor in preparing the dual phase mouthwashes of the invention.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without, departing from the scope of the present invention as defined by the appended claims.

What is claimed is:

1. A lubricating dual-phase mouthwash for the treatment or alleviation of dry mouth comprising:
   a hydrophilic phase;
   a hydrophobic phase comprising at least two oils, wherein the oils comprise coconut oil in an amount of from 0.1%-1% by weight of the composition and mineral oil in an amount of from 5%-15% by weight of the composition, wherein the coconut oil is dispersed in the mineral oil, wherein the hydrophobic phase is from 5% to 20% of the composition by volume;
   a hydrotrope component, wherein the hydrotrope component comprises glycerin and sorbitol;
   wherein the mouthwash is prepared by a process comprising the steps of:
   a) dispersing coconut oil in a hydrophobic composition comprising an oil to form a mixture; and
   b) combining the mixture with the hydrophilic phase and the hydrotrope component, and
   wherein the composition delivers a lubricating effect to the oral cavity.

2. The dual-phase mouthwash according to claim 1, wherein the hydrophobic and hydrophilic phases spontaneously separate following mixing of the phases and are substantially non-emulsified at room temperature at 1 minute following mixing; or at 30 seconds following mixing.

3. The mouthwash of claim 1, wherein the hydrophilic phase comprises the hydrotrope component.

4. The mouthwash of claim 1, further comprising a preservative in amount of from 0.05% to 0.5% by weight.

5. The mouthwash of claim 1, wherein the hydrophilic phase further comprises an antibacterial agent, in an amount of from 0.01-0.1%, or from 0.05%-0.075% by weight.

6. The mouthwash of claim 1, further comprising a fluoride ion source in an amount to provide 1 to 2000 ppm, or 100 to 250 ppm available fluoride; sodium fluoride in an amount of 0.01-0.1%, or 0.05% by weight.

7. The mouthwash of claim 1, further comprising one or more of humectants, flavorings, sweeteners, sensates and/or odor neutralizing agents.

8. The mouthwash of claim 1, further comprising one or more fat-soluble vitamins and/or antioxidants, Co-enzyme Q10, Vitamin E, Vitamin A, Vitamin D and Vitamin K.

9. The mouthwash of claim 1, wherein the hydrophilic phase comprises an effective amount of a preservative.

10. The mouthwash of claim 1, wherein the hydrophilic phase further comprises an acid, an organic acid, or citric acid.

11. The mouthwash of claim 1, wherein:
    each of glycerin and sorbitol is present in an amount of from 5%-10% by weight of the composition.

12. The mouthwash of claim 1, further comprising an optional antibacterial agent, in an amount of from 0%-0.1%, or 0.05%-0.075% by weight; an optional fluoride ion source, sodium fluoride; and citric acid in an amount, of from 0.01% to 0.05% by weight.

13. The mouthwash of claim 1, wherein the two phases are distinct and clear.

14. The mouthwash according to claim 1, wherein the hydrophobic and hydrophilic phases spontaneously separate following mixing of the phases to form two clear and distinct layers at room temperature within 1 minute following mixing; and preferably at 30 seconds following mixing.

15. A method for treating dry mouth comprising contacting the oral cavity of a mammal having dry mouth with a composition according to claim 1.

16. A method for moisturizing the lips of a mammal, comprising contacting the lips of the mammal with a composition according to claim 1.

17. A method of lubricating the oral cavity of a mammal comprising contacting the oral cavity of the mammal with a composition according to claim 1.

18. A method to improve oral health comprising applying an effective amount of the mouthwash of claim 1 to the oral cavity of a subject in need thereof to
- a. reduce or inhibit gingivitis,
- b. promote healing of sores or cuts in the mouth,
- c. inhibit microbial biofilm formation in the oral cavity,
- d. treat, relieve or reduce dry mouth,
- e. enhance systemic health, including cardiovascular health,
- f. reduce erosion of the teeth,
- g. immunize the teeth against cariogenic bacteria and their effects, and/or clean the teeth and oral cavity or
- h. moisturize the lips and/or mouth.

* * * * *

UNITED STATES PATENT AND TRADEMARK OFFICE
CERTIFICATE OF CORRECTION

PATENT NO.        : 10,709,644 B2
APPLICATION NO.   : 15/539192
DATED             : July 14, 2020
INVENTOR(S)       : Stacey Lavender et al.

It is certified that error appears in the above-identified patent and that said Letters Patent is hereby corrected as shown below:

On the Title Page

In item "(72) Inventors", Line 3, delete "Heights," and insert -- Highlands, --, therefor.

In the Specification

In Column 1, Line 19, delete "doe" and insert -- due --, therefor.

In Column 4, Line 2, delete "octenidme)," and insert -- octenidine), --, therefor.

In Column 4, Lines 23-24, delete "monofluorophosphaie," and insert -- monofluorophosphate, --, therefor.

In Column 4, Line 25, delete "fluorosisicate" and insert -- fluorosilicate --, therefor.

In Column 4, Line 26, delete "aftluorosulfate," and insert -- a fluorosulfate, --, therefor.

In Column 6, Line 7, delete "phases, in" and insert -- phases. In --, therefor.

In Column 6, Line 18, delete "11" and insert -- 1 --, therefor.

In Column 6, Line 62, delete "ampiphilic" and insert -- amphiphilic --, therefor.

In Column 7, Line 5, delete "used" and insert -- useful --, therefor.

In Column 7, Line 32, delete "alter" and insert -- after --, therefor.

In Column 8, Line 51, delete "anticalcolus" and insert -- anticalculus --, therefor.

In Column 8, Line 53, delete "copolvols" and insert -- copolyols --, therefor.

Signed and Sealed this
Sixth Day of October, 2020

Andrei Iancu
*Director of the United States Patent and Trademark Office*

CERTIFICATE OF CORRECTION (continued)
U.S. Pat. No. 10,709,644 B2

In Column 8, Line 60, delete "catianic" and insert -- cationic --, therefor.

In Column 9, Line 13, delete "PCX" and insert -- PCT --, therefor.

In Column 9, Line 14, delete "wanning" and insert -- warming --, therefor.

In Column 9, Line 16, delete "vanillvl" and insert -- vanillyl --, therefor.

In Column 9, Line 60, delete "xylitel," and insert -- xylitol, --, therefor.